US012558051B2

(12) United States Patent
Vu

(10) Patent No.: US 12,558,051 B2
(45) Date of Patent: Feb. 24, 2026

(54) SYSTEM AND METHOD OF GENERATING A COLOR-CODED IMAGE DEMONSTRATING BLOOD FLOW

(71) Applicant: Scripps Clinic Medical Group, Inc., La Jolla, CA (US)

(72) Inventor: David Vu, La Jolla, CA (US)

( * ) Notice: Subject to any disclaimer, the term of this patent is extended or adjusted under 35 U.S.C. 154(b) by 305 days.

(21) Appl. No.: 18/222,374

(22) Filed: Jul. 14, 2023

(65) Prior Publication Data

US 2025/0017545 A1     Jan. 16, 2025

(51) Int. Cl.
| | |
|---|---|
| *A61B 6/50* | (2024.01) |
| *A61B 6/00* | (2024.01) |
| *G06T 7/00* | (2017.01) |
| *G06T 19/20* | (2011.01) |

(52) U.S. Cl.
CPC .............. *A61B 6/507* (2013.01); *A61B 6/481* (2013.01); *G06T 7/0016* (2013.01); *G06T 19/20* (2013.01); *G06T 2207/10076* (2013.01); *G06T 2207/30104* (2013.01); *G06T 2219/2012* (2013.01)

(58) Field of Classification Search
CPC ......... A61B 6/481; A61B 6/504; A61B 6/507; G06T 19/20; G06T 2207/10076; G06T 2207/10116; G06T 2207/30104; G06T 2219/2012; G06T 7/0016
See application file for complete search history.

(56) References Cited

U.S. PATENT DOCUMENTS

| | | | |
|---|---|---|---|
| 5,332,968 | A | 7/1994 | Brown |
| 7,886,603 | B2 | 2/2011 | Kamiyama |

| | | | | |
|---|---|---|---|---|
| 8,032,202 | B2 | 10/2011 | Omi et al. | |
| 8,929,632 | B2 * | 1/2015 | Horz ...................... | G16H 50/20 |
| | | | | 382/162 |
| 9,561,011 | B2 | 2/2017 | Arakita et al. | |
| 2006/0215889 | A1 | 9/2006 | Omi et al. | |

(Continued)

FOREIGN PATENT DOCUMENTS

| | | | | |
|---|---|---|---|---|
| AU | 2013200386 | A1 * | 2/2013 | |
| CA | 2802049 | C * | 7/2018 | ......... G01N 33/5308 |

(Continued)

OTHER PUBLICATIONS

J.M Ospel et al. , "Displaying Multiphase CT Angiography Using a Time-Variant Color Map: Practical Considerations and Potential Applications in Patients with Acute Stroke," Nov. 19, 2019, AJNR Am J Neuroradiol 2020, 41 (2), pp. 200-204.).*

(Continued)

*Primary Examiner* — Omar S Ismail

(74) *Attorney, Agent, or Firm* — Schlee IP International; Alexander R. Schlee; Pascal A. Schlee

(57)          ABSTRACT

A method and a system of generating a color-coded image demonstrating blood flow in a chosen area in a patient, specifically for diagnosing medical conditions like ischemia, strokes and infarcts. A plurality of images, preferably 3, are taken at different points in time that are a few seconds apart, and colorized by different colors, preferably a first image red, a second image blue and a third image green. These colorized images are then aligned and summated to create a multicolor image that time encodes perfusion of blood. Preferably, said method is performed after injection of a contrast agent.

26 Claims, 5 Drawing Sheets

(56)                    References Cited

U.S. PATENT DOCUMENTS

| | | | | |
|---|---|---|---|---|
| 2009/0016587 | A1* | 1/2009 | Strobel | G06T 7/20 382/130 |
| 2010/0034441 | A1* | 2/2010 | Makram-Ebeid | A61B 6/481 382/128 |
| 2010/0329526 | A1* | 12/2010 | Pfister | G16H 50/30 382/130 |
| 2011/0235885 | A1* | 9/2011 | Rauch | A61B 6/481 382/131 |
| 2013/0077839 | A1* | 3/2013 | Horz | G06T 11/001 382/130 |
| 2016/0015348 | A1* | 1/2016 | Ohishi | A61B 6/481 600/431 |
| 2016/0048959 | A1* | 2/2016 | Kowarschik | G16H 50/30 600/425 |
| 2016/0051217 | A1* | 2/2016 | Douglas | A61B 6/481 345/419 |
| 2016/0135775 | A1* | 5/2016 | Mistretta | G06T 7/0012 600/419 |
| 2018/0242946 | A1* | 8/2018 | Grbic | A61B 8/58 |
| 2019/0108906 | A1* | 4/2019 | Unser | G06T 7/20 |
| 2019/0380599 | A1 | 12/2019 | Addison et al. | |
| 2020/0034964 | A1* | 1/2020 | Shimamura | G06T 7/20 |
| 2021/0137634 | A1* | 5/2021 | Lang | A61B 90/00 |
| 2021/0321988 | A1* | 10/2021 | Ji | G06T 11/001 |
| 2022/0301227 | A1 | 9/2022 | Kanazawa | |
| 2023/0186474 | A1 | 6/2023 | Kim et al. | |
| 2023/0394657 | A1* | 12/2023 | Noji | G06T 7/11 |

FOREIGN PATENT DOCUMENTS

| | | | | | |
|---|---|---|---|---|---|
| JP | 2010279591 | A | | 12/2010 | |
| KR | 10-2009-0131825 | A | | 12/2009 | |
| KR | 10-2017-0019837 | A | | 2/2017 | |
| KR | 20170019837 | A | * | 2/2017 | A61B 5/026 |
| WO | 2010-086771 | A1 | | 8/2010 | |

OTHER PUBLICATIONS

Kolja M. Thierfelder et al. , "Color-Coded Cerebral Computed Tomographic Angiography Implementation of a Convolution-Based Algorithm and First Clinical Evaluation in Patients With Acute Ischemic Stroke," Nov. 20, 2014, Investigative Radiology , vol. 50, No. 5, May 2015, pp. 361-364.).*

Keith S Cover et al., "Color Intensity Projections: A Rapid Approach for Evaluating Four-Dimensional CT Scans in Treatment Plan," Nov. 20, 2014, Int. J. Radiation Oncology Biol. Phys., vol. 64, No. 3,2006, pp. 954-959.).*

Adrian J. Y. Chee et al. , "Walled Carotid Bifurcation Phantoms for Imaging Investigations of Vessel Wall Motion and Blood Flow Dynamics," Nov. 1, 2016, IEEE Transactions on Ultrasonics, Ferroelectrics, and Frequency Control , vol. 63, No. 11, Nov. 2016, pp. 1852-1857.).*

H. Keigth Brown et al. , "Generation of Color Composites for Enhanced Tissue Differentiation in Magnetic Resonance Imaging of the Brain," Apr. 15, 1991, The American Journal of Anatomy 19223-34 (1991), pp. 23-33.).*

Abigail Swillens et al., Assessment of Numerical Simulation Strategies for Ultrasonic Color Blood Flow Imaging, Based on a Computer and Experimental Model of the Carotid Artery,Aug. 11, 2009,Annals of Biomedical Engineering, vol. 37, No. 11, Nov. 2009, pp. 2188-2197.*

Wu Qiu et al.,"Automated Prediction of Ischemic Brain Tissue Fate from Multiphase Computed Tomographic Angiography in Patients with Acute Ischemic Stroke Using Machine Learning," Mar. 8, 2021, Journal of Stroke,vol. 23, No. 2,May 2021,pp. 234-240.*

Anne Marie Augustin et al.,"Color-coded summation images for the evaluation of blood flow in endovascular aortic dissection fenestration," Feb. 4, 2022, BMC Medical Imaging, vol. 22, Article No. 19( 2022) , pp. 1-6.*

Jakob Nikolas Kather et al.,"Color-coded visualization of magnetic resonance imaging multiparametric maps," Jan. 23, 2017, Scientific Reports ,7:41107,pp. 1-8.*

Tomoya Kobayashi et al.,"Fused CT—Improved image quality of coronary arteries on postmortem CT by summation of repeated scans," May 29, 2020, Forensic Imaging 22( 2020) , 200386,pp. 1-3.*

Anam, C. (2019). "A novel multiple-windows blending of CT images in red-green-blue (RGB) color space: Phantoms study." Scientific Visualization11: 56-69.

Cover, K. S., et al. (2006). "Color intensity projections: a rapid approach for evaluating four-dimensional CT scans in treatment planning." Int J RadiatOncol Biol Phys64(3): 954-961.

Ospel, J. M., et al. (2020). "Displaying Multiphase CT Angiography Using a Time-Variant Color Map: Practical Considerations and Potential Applications in Patients with Acute Stroke." AJNR Am J Neuroradiol41(2): 200-205.

Kobayashi, T. (2020). "Noise reduction effect of computed tomography by image summation method (fused CT): Phantom study, ." Forensic Imaging23.

Kobayashi, T. (2020). "Fused CT-Improved image quality of coronary arteries on postmortem CT by summation of repeated scans." Forensic Imaging22.

Qiu, W., et al. (2021). "Automated Prediction of Ischemic Brain Tissue Fate from Multiphase Computed Tomographic Angiography in Patients with Acute Ischemic Stroke Using Machine Learning." J Stroke23(2): 234-243.

* cited by examiner

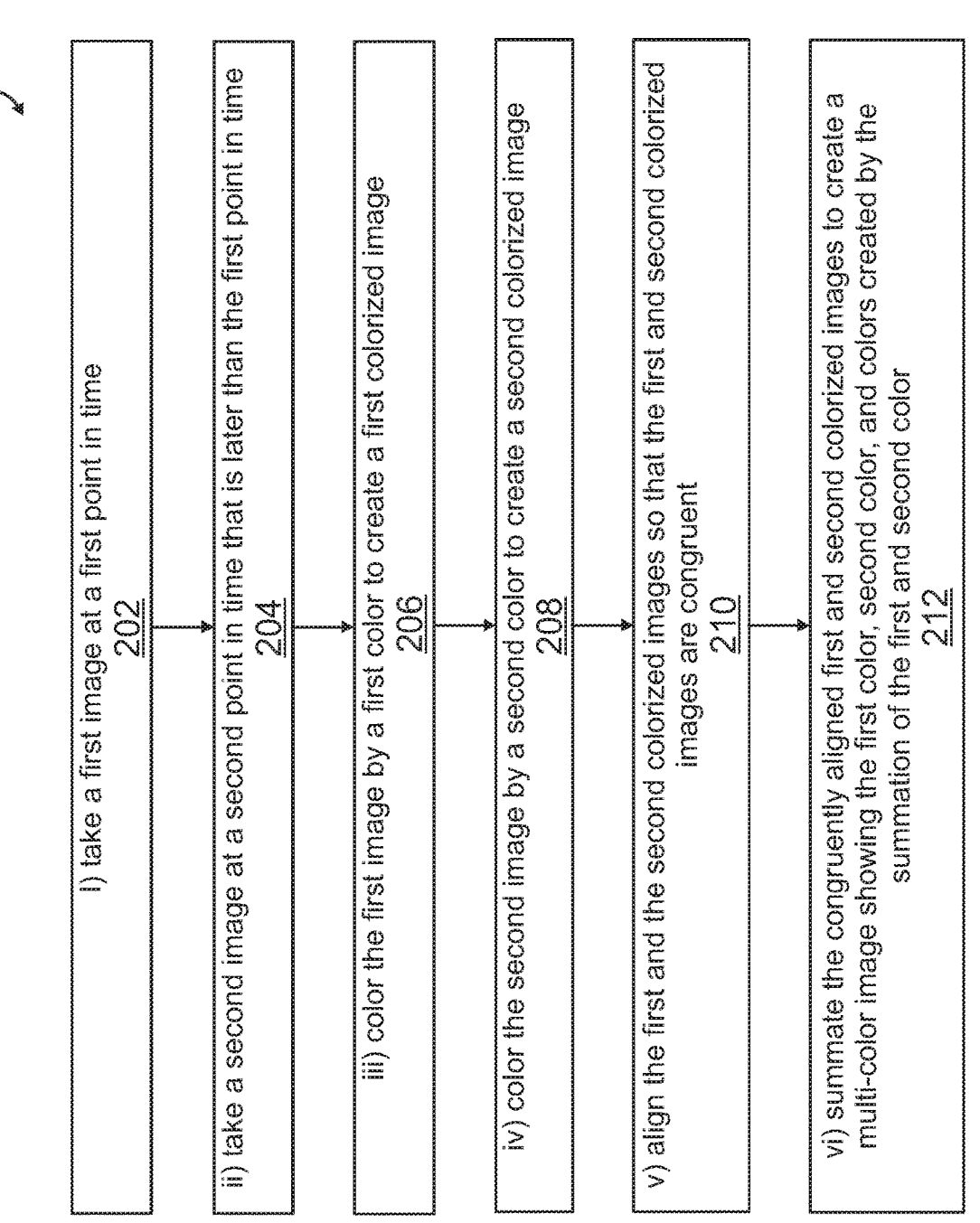

i) take a first image at a first point in time
202 ii) take a second image at a second point in time that is later than the first point in time
204 iii) color the first image by a first color to create a first colorized image
206 iv) color the second image by a second color to create a second colorized image
208 v) align the first and the second colorized images so that the first and second colorized images are congruent
210 vi) summate the congruently aligned first and second colorized images to create a multi-color image showing the first color, second color, and colors created by the summation of the first and second color
212

FIG 2

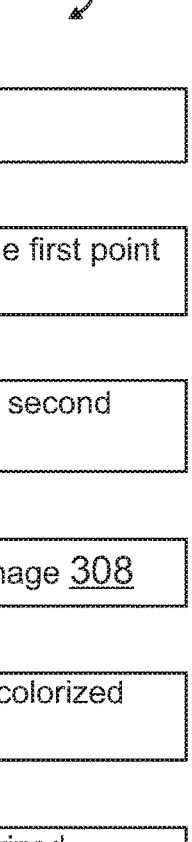

300

I) take a first image at a first point in time 302 ii) take a second image at a second point in time that is later than the first point in time 304 iii) take a third image at a third point in time that is later than the second point in time 306 iv) color the first image by a first color to create a first colorized image 308 v) color the second image by a second color to create a second colorized image 310 vi) color the third image by a third color to create a third colorized image 312 vii) align the first, second and third colorized images so that the first, second and third colorized images are congruent 314 vii) summate the congruently aligned first, second and third colorized images to create a multi-color image showing the first color, second color, third color and colors created by the summation of the first, second and third colors 316

FIG. 3

SYSTEM AND METHOD OF GENERATING A COLOR-CODED IMAGE DEMONSTRATING BLOOD FLOW

TECHNICAL FIELD

The invention relates to a system and a method of generating a color-coded image demonstrating blood flow in a chosen area in a patient.

BACKGROUND

Various systems and methods are known for processing a plurality of images. For example, the Japanese patent application publication JP 2010279591 A teaches a medical image diagnostic apparatus and program determining a difference between three sheets of images. A storage part of a viewer stores three medical image data obtained by photographing the same one region in a subject at different times and dates. A data converting part converts three medical image data to primary color image data different in color. A data synthesizing part synthesizes the image data of the three primary colors to generate synthetic image data. An image is generated based on the synthetic image data.

However, although this system and method can visually demonstrate the difference between three static images taken at any given point in time, for example, by summating 3 images for better highlighting the appearance of tumors, no encoding of time in color was envisaged. In short, this method and system has no dynamic capabilities, and is therefore unsuitable for demonstrating any dynamic events, such as desirable for imaging conditions related to blood flow, for example ischemia and infarcts. Perfusion is defined as the passage of fluid through vessels and arteries, while the term infarct implies tissue death due to Ischemia, the latter being defined as insufficient oxygen.

Other systems and methods are known that summate monochromatic images of different colors, for example from the U.S. Pat. No. 5,332,968 A assignments of primary and nonprimary colors to a plurality of images to make a final image generated by summation look like living tissue.

From the U.S. Pat. No. 9,747,700 B2 colorizing and/or standardizing a medical image is known teaching to assign the entire color spectrum to CT gray scale. Histograms of densities are used to assign colors to exaggerate subtle differences by use of color. This method colorizes an image on a pixel by pixels basis to make subtle differences more visible, but like all other aforementioned methods does not envisage encoding time in color and therefore has no dynamic aspects.

Further, from the commercial product Syngo iFlow® (Siemens Healthcare GmbH, Erlangen, Germany) colorizing catheter angiograms is known, colorizing intracranial vessels on catheter angiograms to show the passage of time. Various parameters like time to peak and transit time are measured, and pixel by pixel calculations are performed, assigning colors on a pixel by pixel basis, in contrast to colorizing the whole image. This process is computationally complex and susceptible to noise.

Although colorization is known as such in radiology, be it on a pixel by pixel basis or by using algorithms or by image summation of images of different colors, all of these prior art systems and methods do not encode the passage of time by color summation.

There is a need to show perfusion maps demonstrating blood flow in areas of interest in a conspicuous, color coded manner, preferably with minimal computation time and computation complexity. Specifically there is a need for a simple and effective computation of such perfusion maps color coding time, e.g. demonstrating at what point in time the blood flow reached certain areas in a patient, for example within the brain or in other blood vessels, for instance to identify blood vessels suffering from partial or full clogging. This helps diagnosing ischemia, infarcts and strokes in a more precise and faster fashion. In this connection it is desirable to keep computation simple and fast, which may also reduce noise and therefore increase visibility of even smaller infarcts.

SUMMARY OF THE INVENTION

According to a first aspect of the invention, a method generates a color-coded image demonstrating blood flow in a chosen area in a patient, said method comprising: i) taking a first image at a first point in time; ii) taking a second image at a second point in time that is later than the first point in time; iii) coloring the first image by a first color to create a first colorized image; iv) coloring the second image by a second color to create a second colorized image; v) aligning the first and the second colorized images so that the first and second colorized images are congruent; vi) summating the congruently aligned first and second colorized images to create a multicolor image showing colors created by the summation of the first and second color.

According to a second aspect of the invention a system takes and processes images for demonstrating blood flow in a chosen area in a patient by generating a color-coded image demonstrating such blood flow, said system comprising: an imaging device configured to take images of the chosen area in a patient including at least a first image at a first point in time and a second image at a second point in time, wherein the first and second points in time are set apart by 1 s-10 s; a computer programmed to: color the first image with a first color to create a first colorized image and the second image with a second color to create a second colorized image; align the first and the second colorized images so that the first and second colorized images are congruent; and summate the congruently aligned first and second colorized images generating a multicolor image showing colors created by the summation of the first and second color; and a display device displaying the multicolor image.

DETAILED DESCRIPTION OF THE INVENTION

Briefly summarizing, the process according to the invention includes (1) capturing plural temporally separated CT slices at the same Z-value, (2) assigning a different primary color to each of the separated CT slices, (3) laterally aligning, superposing, and adding the three slices to generate an RGB plot, and (4) using superposed/added color to identified delayed blood flow by a shift toward the temporally delayed primary color.

Depending on the different areas to be examined within a patient, or difference in blood flow velocity from patient to patient, for example based on age, the time by which the different images are captured can be varied. Also, the time offset between taking the first image and the second image can differ from the time offset between taking the second and the third image.

Although depending on the specific application it may be useful for more than 2 or 3 images to be taken, it turned out 3 images and using a RGB color scheme for the 3 images yielded good results at low complexity. The sequence of the colors 1) red, 2) blue and 3) green is preferred, but in the alternative, also an RGB sequence would also be suitable. Also, other colors may be used.

If the invention is used with a contrast agent, 3 separate images or image stacks are obtained at three time points that have dynamically injected IV contrast, and colored red, blue and green. Summing up the 3 images, a composite multi-color image is generated encoding the passage of time onto the static image and visualizing:

i. Tissue perfusion, thus allowing the diagnosis of early strokes;

ii. Abnormally delayed blood flow in the intracranial vessels or elsewhere, thus localizing intravascular clots and areas of narrowing; and iii. Complex vascular malformations or structures in a single image without the need to review a video loop.

Although possible, no other colors or color spectrums need to be assigned. The color summation generates all other colors. In contrast to prior art pixel by pixel approaches, the method according to the invention does not include assigning specific colors or locations of such colors within an image. For example, superimposing the colors red and green at specific ratios creates the color orange, but prior to superimposing these 2 colors, it is not known where in the image the color orange will show, or even whether the multicolor image will show any orange.

A primary color is assigned to each one of the entire images to be combined by summation, in contrast to selecting just one region of the image to colorize. Aside from addition of the three images, no other math used, e.g. no calculation of histograms, deconvolution, or calculus, which distinguishes the present technique from those used in commercial products.

Using the invention with dynamically injected contrast is the most common scenario, for example for CT angiograms and catheter angiograms. Also, the use in MR angiograms, barium studies, interventional fluoroscopic procedures that use contrast or devices that are visible on X ray, ultrasound (when ultrasound contrast is used) or when there is motion during the ultrasound procedure is possible.

The invention is also applicable in dynamic systems that do not use injected contrast. For example, some MRI techniques see moving blood or CSF without injected contrast.

An advantage of the invention is decreasing noise by the summation of a plurality of images by creating a better signal-to-noise ratio in the composite images created by summation, so that also smaller and more faint objects are more visible. This is important as many strokes are only slightly different in appearance from normal tissue. Although the method according to the invention is quite simple from a computational standpoint, it does require exact alignment of the images to be combined to the composite image, but this has shown to be accomplishable, even overcoming motion by or within the patient.

In the following, an example of applying the invention for a head CT is discussed step by step in more detail:

1. Three data sets are used for colorization, namely: 1) Head and neck CT angiogram which is scanned in the arterial phase, 2) After a time delay 1 a head CT angiogram in the venous phase, and 3) After a time delay 2 head CT angiogram which is scanned in the late phase.

2. The arterial phase CT series contains both head and neck images together. The neck images need to be removed first. This can be accomplished by first arbitrarily designating a reference stationary head CT which has only head CT images. For this purpose, the scan after time delay 1 can be used. The computer counts how many images this scan contains. The scan with a much larger total number of images is the one which contains neck images. The program takes this scan and keeps only the top number of slices equal to the number of images on the delay 1 head CT. By this process, the computer algorithm can subtract out the neck images.

3. All three CT series now have the same number of slices. However, they all still have images of the head holder device in the scan, which also must be removed to allow proper alignment of just the head CT. This sequence may be programmed by using existing functions inside 3D slicer, an open source software program. The invention can be implemented as a new software module in the programming language Python to work inside the open source software program called 3D Slicer. The program applies a threshold cut-off that keeps only objects above a certain density. This process captures both the head and the head holder device. Then the program runs the known "keep the largest island" function. This will keep only the head since the device is always smaller than the head and is not continuous with the head. The head holder device is thus removed.

4. CT head images are now aligned by applying the appropriate software, such as Elastix, a publicly available open source software which is built inside 3D slicer. The program launches this software which moves each head CT to match the user designated stationary head CT. It does this by translation in three axes and rotation in three axes and uses a loss function with an aim to minimize the loss function. After this step, all three head CTs are aligned.

5. Now the best window and level to view the images is chosen. This is done by an interface allowing the user to choose a window and level to view in the gray scale images. While the interface was created for practical use of the instant invention, the window leveling is a preexisting function. For this example, a window level has been chosen that best shows the brain parenchyma or the blood vessels (window level: 35 and 70 for brain and 250 and 1000 for the vessels, but these numbers can be chosen differently depending on the specific application. The chosen window level accomplishes that the images show a wide range of gray values. The same window and levels are applied to all three CT series.

6. Each head CT is now colorized. Each head CT is already a gray scale image. Each gray pixel is created by sub pixels that are equally red, green, and blue light but set at an intensity level of less than 100 percent luminosity, which results in gray rather than white as would be the case if all intensities are set at a 100 percent luminosity. To color the first head CT red, the computer program simply turns off the blue and green subpixels by setting blue and green to equal zero. The resulting image looks red. This is repeated with the appropriate colors set to zero for the other two scans to create the green and blue images.

7. The three colored CT scans are simply overlaid to set the intensity of each subpixel inside an image pixel. This will give the impression of color "summation" via the physiological perception of color mixing by the human retina.

By applying the colors in the sequence of red for the first image, blue for the second image taken after the time delay 1 from taking the first image, and then green as the third color and last color after time delay 2 the resulting summed image appears multicolored where areas that are more red in appearance have early blood flow. Areas that are more green in appearance are areas due to delayed blood flow. By looking for color asymmetry, it is possible to quickly decide if the blood flow is normal and balanced or abnormal with green colors indicating delayed or impaired blood flow.

One of the main applications is for finding acute stroke. Strokes often occur due to a blood clot impeding blood flow to a part of the brain. On colorized CT, areas of the brain with strokes appear green due to delayed contrast arrival. Normal brain, on the other hand, appears purple since it gets flow during the early phases (red and blue phases) of the contrast injection.

Besides seeing the brain tissue, this technique also visualizes the blood vessels and so the head arteries also appear purple if normal but appear green when abnormal. These colors allow a reader to determine "at a glance" if the scan is normal or not. And if it is abnormal, then the reader instantly knows where the abnormality is located, and which vessel is abnormal and responsible for the stroke.

While this technique is useful in stroke, it can be applied in any area of the body with three separate images obtained sequentially during administration of contrast material. For some liver and neck tumors, the different pattern of injected IV contrast arrival time helps diagnose tumor types. Therefore, different tumors will have a different "color signatures" that help indicate tissue type, and this will be visible by this technique. For other medical situations like in catheter angiograms, the colorization of the images allows a single concise depiction of how injected contrast moves through a complex network of blood vessels at different time points. This makes diseases with complex vessel anatomy much easier to comprehend for diagnosis and treatment. This technique also works for ingested oral contrast in fluoroscopic images. Colorization can depict how oral contrast moves through the body.

The acute stroke CT protocol according to the invention is to scan the head at three successive time points, each separated by a few seconds, while rapidly injecting IV contrast. These three sets of head CT images are gray scale images and are in a DICOM file format. For the CT image at time point 1, according to an alternative embodiment, each gray scale pixel in the image is then assigned to a corresponding red color and brightness by what is called a "lookup table". This is repeated for images in time points 2 and 3 and these gray scale images will be assigned colors from the blue and green "lookup table" respectively. The CT images are then aligned to correct for motion. They are resized to correct for different magnification. This allows the images to perfectly overlap. In the alternative to using a lookup table, it is preferable to simply turn of sub-pixels, as described above, for achieving the effect of colorizing the respective images taken at different points in time.

The images are then overlapped and presented on a color monitor. Each pixel in the color monitor has three sub-pixels of red, green, or blue. The displayed intensity of each sub-pixel is determined by the underlying red, green and blue color intensities for that pixel location from the three source images taken at time points 1, 2 and 3. The human retina will do the color summation, meaning that the appearance of colors aside from red, green, and blue are due to the eye interpreting the three inputs as a unique color. For example, a yellow color is from an equal balance of red and green light. A spectroscopic measurement of a yellow color in the composite image, for example, will not correspond to a wavelength of yellow in the electromagnetic spectrum. Instead, it will reveal two equal, sharp peaks at the wavelengths for red and green. However, to the human eye it will look yellow.

The brightness and contrast settings of the underlying gray scale image have a significant impact on the final color. The brightness and contrast settings are chosen to best depict the subtle changes of stroke. The same settings are applied for the three CT images from the three different time points.

The following lists some additional advantages of the instant invention:

1. The method according to the invention allows to extract new information from data that is already being obtained. There is no need for extra radiation or additional contrast injection to obtain significantly more data in acute strokes.

2. The method according to the invention can for example cover the entire brain, which is something other CT perfusion techniques try to avoid in order to limit radiation dose.

3. The method according to the invention colorizes the vessels directly to show which vessels are causing the stroke in a way that is much easier and more robust than with other techniques like ColorViz that do not have the full range of colors applied to the vessels and instead has discrete colors.

4. The method according to the invention sums three sequential images and so the signal-to-noise ratio is better. Thus, smaller structures and more subtle variations reflecting early strokes can be seen.

5. The method according to the invention uses only three scans to generate a map that is comparable to perfusion. Official perfusion takes many more scans and thus are more motion sensitive. Therefore, this technique is less susceptible to motion artifacts.

6. The method according to the invention is applicable to a number of medical diagnoses, such as diagnosing strokes, abdominal tumors, diagnosis of gastrointestinal, urinary, vascular dysfunction or malformation throughout the body.

BRIEF DESCRIPTION OF THE DRAWINGS

FIG. 2 shows a block diagram demonstrating the method according to the invention applying 2 colors;

FIG. 3 shows a block diagram demonstrating the method according to the invention applying 2 colors;

DETAILED DESCRIPTION OF THE DRAWINGS

Figure 1:
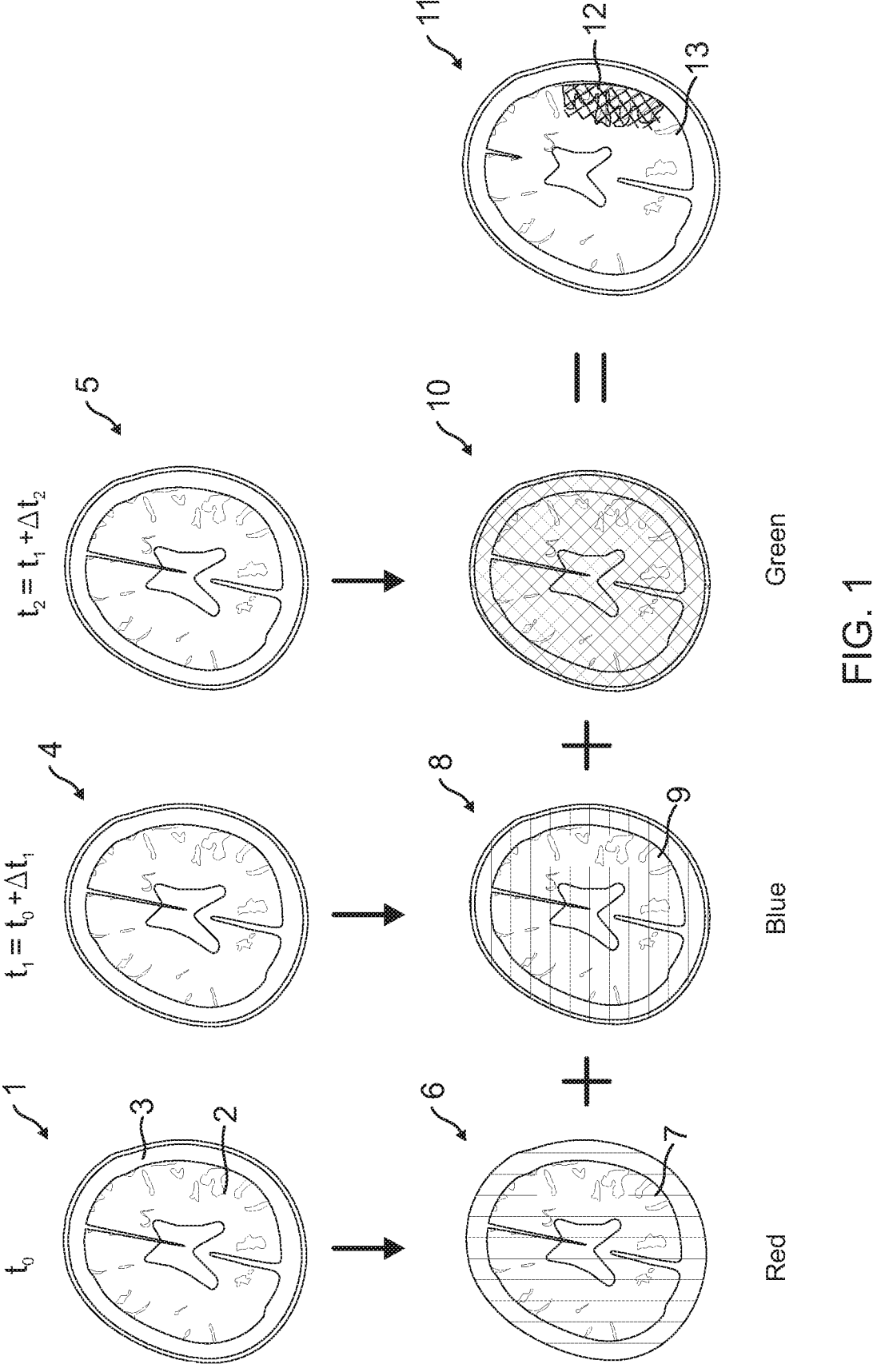
FIG. 1 demonstrates generating a multicolor image generated according to the invention to color an area where a stroke happened.
Figure 4:
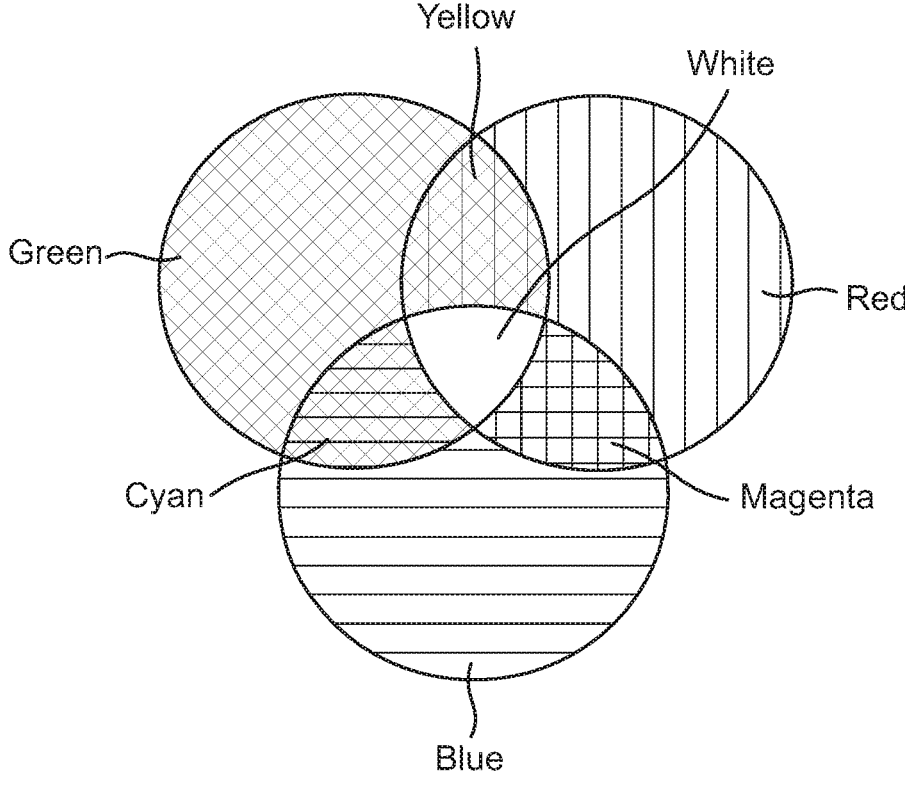
FIG. 4 depicts the principle of color summation and the resulting colors generated.

FIG. 1 shows how this color summation principle demonstrated in FIG. 4 is applied according to the invention on coloring a CT for demonstrating blood flow in a brain 2 of a patient, specifically a patient who has suffered a stroke. After injection of a contrast agent, at a first point in time $t_0$ a first image 1 is generated by the CT scan. CT scans generate gray scale images. The outer white rim shows the skull 3 white due to comprising dens bone.

After a delay $\Delta t_1$ a second image 4 is taken at the point in time $t_1 = t_0 + \Delta t_1$, like all CT images in gray scale. As the blood marked by the contrast agent perfuses through the brain, the image 4 differs from the image 1 in that the blood flow has meanwhile progressed during the time $\Delta t_1$ that has lapsed between the point in time $t_0$ when the first image 1 was taken and point in time $t_1$ when the second image 4 was taken.

Finally, at the point in time $t_2 = t_1 + \Delta t_2$ a third image 5 was taken after a second delay in time $\Delta t_2$. $\Delta t_2$ could be equal to $\Delta t_1$, longer than $\Delta t_1$ or shorter than $\Delta t_1$. However, both $\Delta t_1$ and $\Delta t_2$ are in a range of a few seconds, for example 3 seconds, for capturing the progress of the perfusion.

Coloring the first image 1 red generates the red colored image 6. The red color is coded by a first hatching 7 demonstrating the color red.

Coloring the second image 2 blue generates the blue colored image 8. The blue color is coded by a second hatching 9 demonstrating the color blue.

Coloring the third image 5 green generates the green colored image 10. The blue color is coded by a third hatching 14, which is a crosshatching, demonstrating the color green.

Next, the colored images 6, 8 and 10 are summated, resulting in the multicolor image 11. An area where the blood flow arrives last shows predominantly or exclusively green, namely blood that only arrived in the respective area at the last point in time, denoted by reference numeral 12. The remaining area shows typically in some shade of purple generated by the summation of the colors red and blue, meaning that the blood arrived in these areas 13 sooner than in the area 12. Although the resulting multicolor image 11 should show all 3 hatchings (vertical hatching, horizontal hatching and crosshatching), demonstrating all 3 colors at different intensities in different areas in the multicolor image 11, for simplicity only the green hatching is shown, showing the area 13 where the blood flow arrived last and which might indicate ischemia or stroke. The general concept of color summation is demonstrated in FIG. 4. Notably, the colorized images 6 and 8 colorized red and blue do not show any hatchings in the area designated 12 in the multicolor image 11 showing green. In an embodiment where a contrast agent is used, this contrast agent has not or has only insufficiently arrived at the area 12 at the times $t_0$ and $t_1$, and substantially arrived there at the time $t_2$, which is color-coded green. If by the time $t_2$ all the contrast agent that was present at time $t_0$ and $t_1$ has vanished, then only the area 12 shows green and should show crosshatching in the colorized image 10, like in the multicolor image 11. In case there is some overlap, meaning some of the contrast agent present at respective areas at the times $t_0$ and $t_1$ is still present at time $t_2$, a resulting mixed color would show in such areas. FIG. 1 is a simplified depiction for demonstrating the main effects that are accomplished by the colorizing and color summation, but it needs to be understood that in practical applications, several different color shades show throughout the multicolor image 11, not just in one area 12 that is green or predominantly green as in the discussed embodiment.

The image 11 allows the doctor or other medical technician to identify problematic areas, for example ischemic tissue or tissue where a stroke has happened. In contrast, if no medical condition is present, the color is balanced.

Of note, the skull 3 shows white also in the multicolor image 11 due to the high bone density of the skull, hiding the contrast agent that would otherwise show in the skull area and demonstrate blood flow in the skull marrow.

FIG. 2 shows a flowchart listing the steps for combining two images to generate a color-coded multicolor image demonstrating blood flow in a chosen area in a patient, according to method 200.

In step 202, a first image 1, 501 may be taken at a first point in time.

In step 204, a second image 4, 504 may be taken at a second point in time that is later than the first point in time.

In step 206, the first image 1, 501 may be colored a first color, thereby creating a first colorized image 6, 506.

In step 208, the second image 4, 504 may be colored a second color, thereby creating a second colorized image 8, 508.

In step 210, the first colorized image 6, 506 and the second colorized image 8, 508 may be aligned so that the first colorized image 6, 506 and second colorized image 8, 508 are congruent.

In step 212, the congruently aligned first colorized image 6, 506 and second colorized image 8, 508 may be summated to create a multicolor image 11, 511 showing colors created by the summation of the first color and second color. In areas where the intensity of the second color is zero, the color created by the color summation is the first color, which conversely, in areas where the intensity of the first color is zero, the color created by the color summation is the second color.

FIG. 3 shows a flowchart listing the steps for combining three images to generate a color-coded multicolor image demonstrating blood flow in a chosen area in a patient, according to method 300.

In step 302, a first image 1, 501 may be taken at a first point in time.

In step 304, a second image 4, 504 may be taken at a second point in time that is later than the first point in time.

In step 306, a third image 5, 505 may be taken at a third point in time that is later than the second point in time.

In step 308, the first image 1, 501 may be colored a first color, thereby creating a first colorized image 6, 506.

In step 310, the second image 4, 504 may be colored a second color, thereby creating a second colorized image 8, 508.

In step 312, the third image 5, 505 may be colored a third color, thereby creating a third colorized image 10, 510.

In step 314, the first colorized image 6, 506, the second colorized image 8, 508, and the third colorized image 10, 510 may be aligned so that the first colorized image 6, 506, the second colorized image 8, 508, and the third colorized image 10, 510 are congruent.

In step 316, the congruently aligned first colorized image 6, 506, second colorized image 8, 508, and third colorized image 10, 510 may be summated to create a multicolor image 11, 511 showing colors created by the summation of the first, second, and third colors. In areas where the intensities of the first and second color are zero, the color created by the color summation—as perceived by the retina of the human eye—is the third color. In areas where the intensities of the second and third colors are zero, the color created by the color summation is the first color. Finally, in areas where the intensities of the first and third colors are zero, the color created by the color summation is the second color. However, it is possible that some level of intensities of all three colors are present in all areas, in which case the pure first, second and third colors do not show in the multicolor image created by color summation, just mixed colors throughout the multicolor image, including the color white in areas where all 3 colors are present at the same intensities.

FIG. 4 depicts the principle of color summation and the resulting colors generated. As shown in FIG. 4, it is assumed that the light intensity of all three colors red, green and blue are approximately the same. Superimposing green and blue light at approximately the same light intensities creates the color cyan, red and blue the color magenta, and green and red the color yellow. Summating all three colors at approximately the same light intensities creates the color white. In FIG. 4, the white area in the middle should show the hatchings demonstrating all three colors by vertical hatching, horizontal hatching and crosshatching, but it is left white for better demonstration of the color white.

Figure 5:
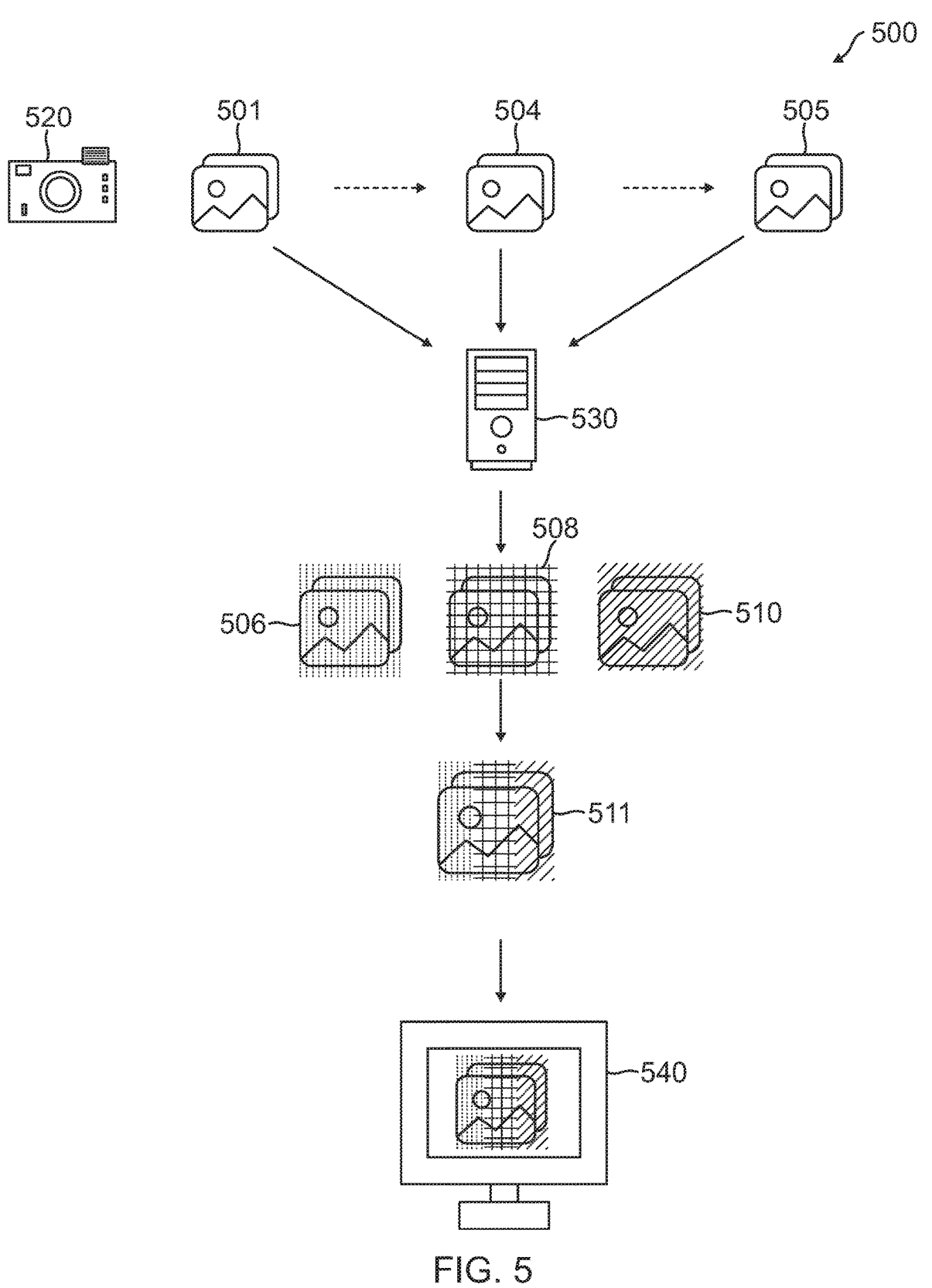
FIG. 5 is a schematic diagram of a system for generating a multicolor image generated according to the invention for visualizing blood flow in a patient.

FIG. 5 shows system 500 for taking and processing images for demonstrating blood flow in a chosen area in a patient by generating a color-coded multicolor image 511 demonstrating such blood flow. The system 500 may include an imaging device 520 configured to capture a plurality of images, for instance a first image 501, a second image 504, and a third image 505. In a preferred embodiment, the imaging device 520 is a computed tomography (CT) scanner configured to obtain detailed internal images of a patient's body. However, the imaging device 520 may alternatively be any imaging apparatus suitable for imaging relevant parameters of a body.

The plurality of images 501, 504, 505 is taken at temporally-spaced intervals, for example with intervening time delays between one second and ten seconds, but for certain applications a greater or lesser time delay may be advantageous. Each of the images 501, 504, 505 captures the same area of the patient's body, such that the images 501, 504, 505 may subsequently be overlaid in order to visually represent changes over time.

The plurality of images 501, 504, 505 may be transmitted from the imaging device 520 to a computer 530 in a conventional manner. The computer 530 may be configured to perform a sequence of functions on the images received from the imaging device 520. First, the computer 530 may colorize each of the images with a respective color. The first image 501 may for instance be colorized red (denoted by a dot pattern), thereby generating a first colorized image 506. The second image 504 may for instance be colorized blue (denoted by a plaid pattern), thereby generating a second colorized image 508. The third image 505 may for instance be colorized green (denoted by a diagonal stripe pattern), thereby generating a third colorized image 510. Next, the first colorized image 506, the second colorized image 508, the third colorized image 510 are overlaid such that common elements between the images are aligned. Subsequently, a multicolor image 511 is generated by summating the respective colorized images 506, 508, 510.

The multicolor image 511 may be transmitted from the computer 530 to a display device 540 in a conventional manner. The multicolor image 511 may be displayed on the display device 540, where it may for instance be viewed and analyzed by a healthcare professional.

In the following, additional embodiments of the invention are described:

Embodiment 1. An embodiment of a method of generating a color-coded multicolor image demonstrating blood flow in a chosen area in a patient, said method comprising:

i) taking a first image 1, 501 at a first point in time to;

ii) taking a second image 4, 504 at a second point in time $t_1$ that is later than the first point in time to;

iii) coloring the first image 1, 501 by a first color to create a first colorized image 6, 506;

iv) coloring the second image 4, 504 by a second color to create a second colorized image 8, 508;

v) aligning the first and the second colorized images 6, 8 so that the first and second colorized images 6, 506; 8, 508 are congruent;

vi) summating the congruently aligned first and second colorized images 6, 506; 8, 508 to create a multicolor image 11, 511 showing the first color, second color, and colors created by the summation of the first and second color.

Embodiment 2. The method according to embodiment 1, further comprising:

vii) taking a third image 5, 505 at a third point in time $t_2$ that is later than the second point in time $t_1$;

viii) coloring the third image 5, 505 by a third color to create a third colorized image 10;

ix) aligning the first, second and third colorized images 6, 506; 8, 508; 10, 510 so that the first, second and third colorized images 6, 506; 8, 508; 10, 510 are congruent;

x) summating the congruently aligned first, second and third colorized images 6, 506; 8, 508; 10, 510 to create a multicolor image 11, 511 showing the first color, second color, third color and colors created by the summation of the first, second and third colors.

Embodiment 3. The method according to embodiment 1, wherein the first color is red and the second color is blue.

Embodiment 4. The method according to embodiment 2, wherein the first color is red, the second color is blue, and the third color is green.

Embodiment 5. The method according to embodiment 4, wherein no additional images beyond the first, second and third colorized images 6, 506; 8, 508; 10, 510 are summated.

Embodiment 6. The method according to any one of embodiments 1-5, wherein the entire respective images are colorized by the respective colors.

Embodiment 7. The method according to any one of embodiments 1-6, wherein the summation of the colorized images 6, 8, 10 is a plain summation without applying any other mathematical algorithms such as calculation of histograms, deconvolution, or application of calculus.

Embodiment 8. The method according to any one of embodiments 1-7, wherein the images are taken at subsequent points in time that are between 1 and 10 seconds apart from each other.

Embodiment 9. The method according to any one of embodiments 1-8, further comprising injection of a contrast agent prior to performing any of the steps i) through x).

Embodiment 10. The method according to embodiment 9, wherein the method is applied in one of a group consisting of: CT angiograms, catheter angiograms, MR angiograms, barium studies, interventional fluoroscopic procedures that use contrast, and ultrasound with the use of ultrasound contrast.

Embodiment 11. The method according to any one of embodiments 1-8, wherein the method is an interventional fluoroscopic procedure including devices that are visible on X-ray.

Embodiment 12. The method according to any one of embodiments 1-8, wherein the method is an ultrasound procedure in connection with motion.

Embodiment 13. The method according to any one of embodiments 1-8, wherein the method is applied in dynamic systems that do not use injected contrast agents.

Embodiment 14. The method according to embodiment 13, wherein the method is applied in MRI techniques making moving blood or CSF visible.

Embodiment 15. The method according to embodiment 10, wherein the method is applied to a gray scale image where each gray pixel is created by subpixels of red, green, and blue light of different intensity levels of less than 100 percent luminosity resulting in gray rather than white as would be the case if all intensities are set at a 100 percent luminosity, wherein for coloring the first image 1, 501 red, a computer program coloring algorithm turns off the blue and green subpixels by setting blue and green subpixel light intensities to zero;

for coloring the second image 4, 504 blue, a computer program coloring algorithm turns off the red and green subpixels by setting red and green subpixel light intensities to zero; and for coloring the third image 5, 505 green, a computer program coloring algorithm turns off the red and blue subpixels by setting red and blue subpixel light intensities to zero.

Embodiment 16. A system for taking and processing images for demonstrating blood flow in a chosen area in a patient by generating a color-coded multicolor image demonstrating such blood flow, said system comprising:

an imaging device 520 configured to take images of the chosen area in a patient including at least a first image 1, 501 at a first point in time to and a second image 4, 504 at a second point in time t₁, wherein the first and second points in time are set apart by 1 s-10 s;

a computer 530 programmed to:

color the first image 1, 501 with a first color to create a first colorized image 6, 506 and the second image 4, 504 with a second color to create a second colorized image;

align the first and second colorized images so that the first and second colorized images 6, 506; 8, 508 are congruent; and summate the congruently aligned first and second colorized images 6, 506; 8, 508 generating a multicolor image 11, 511 showing the first color, second color, and colors created by the summation of the first and second color; and a display device 540 displaying the multicolor image 11, 511.

Embodiment 17. The system according to embodiment 16, wherein said imaging device 520 is configured to take a third image 5, 505 at a third point in time t₂ that is set apart from second point in time t₁ by 1 s-10 s; and said computer 530 is further programmed to:

color the third image 5, 505 with a third color to create a third colorized image 10;

align the first, second and third colorized images 6, 506; 8, 508; 10, 510 so that all 3 images are congruent; and summate the congruently aligned 3 colorized images generating a multicolor image showing the first, second and third colors and colors created by the summation.

Embodiment 18. The system according to embodiment 16, wherein the computer 530 is programmed to color the first image 1, 501 red and the second image 4, 504 blue.

Embodiment 19. The system according to embodiment 17, wherein the computer 530 is programmed to color the first image 1, 501 red, the second image 4, 504 blue and the third image 5, 505 green.

Embodiment 20. The system according to embodiment 19, wherein the computer 530 is programmed to summate just the first, second and third colorized images 6, 506; 8, 508; 10, 510 and no additional images and to color all three images in their entirety by the respective colors.

Embodiment 21. The system according to any one of embodiments 16-20, wherein the summation of the colorized images is a plain summation without applying any other mathematical algorithms such as calculation of histograms, deconvolution, or application of calculus.

Embodiment 22. The system according to any one of embodiments 16-21, further comprising an injection apparatus configured to inject a contrast agent into the patient prior to taking images by the imaging device 520.

Embodiment 23. The system according to embodiment 22, wherein the imaging device 520 is one of a group consisting of: CT angiogram imaging device, catheter angiogram imaging device, MR angiogram imaging device, barium studies imaging device, interventional fluoroscopic procedures imaging device that use contrast, and ultrasound imaging device with the use of ultrasound contrast.

Embodiment 24. The system according to any one of embodiments 16-21, wherein the imaging device 520 is an interventional fluoroscopic procedure imaging device including devices that are visible on X-ray.

Embodiment 25. The system according to any one of embodiments 16-21, wherein the imaging device 520 is an ultrasound procedure imaging device configured to image in connection with motion.

Embodiment 26. The system according to any one of embodiments 16-21, wherein the imaging device 520 is applied in dynamic systems that do not use injected contrast agents.

Embodiment 27. The system according to embodiment 26, wherein the imaging device 520 is an MRI imaging device configured to making moving blood or CSF visible.

Embodiment 28. The system according to any one of embodiments 19-23, wherein the method is applied to a gray scale image where each gray pixel is created by subpixels of red, green, and blue light of different intensity levels of less than 100 percent luminosity resulting in gray rather than white as would be the case if all intensities are set at a 100 percent luminosity, wherein the computer 530 is further programmed to perform a computer program coloring algorithm for coloring said first, second and third images by:

for coloring the first image 1, 501 red, said computer program coloring algorithm turning off the blue and green subpixels by setting blue and green subpixel light intensities to zero;

for coloring the second image 4, 504 blue, said computer program coloring algorithm turning off the red and green subpixels by setting red and green subpixel light intensities to zero; and for coloring the third image green, said computer program coloring algorithm turning off the red and blue subpixels by setting red and blue subpixel light intensities to zero.

The following is a list of reference numerals as shown in the drawings:

1 first image
2 brain
3 skull
4 second image
5 third image
6 first colorized image

13

7 first hatching
8 second colorized image
9 second hatching
10 third colorized image
11 multicolor image
12 first area
13 second area
14 third hatching
200 method
202 method step
204 method step
206 method step
208 method step
210 method step
212 method step
300 method
302 method step
304 method step
306 method step
308 method step
310 method step
312 method step
314 method step
316 method step
318 method step
500 system
501 first image
504 second image
505 third image
506 first colorized image
508 second colorized image
510 third colorized image
511 multicolor image
520 imaging device
530 computer
540 display device

What is claimed is:

1. A method of generating a color-coded multicolor image demonstrating blood flow in a chosen area in a patient, said method comprising:
   i) taking a first image at a first point in time;
   ii) taking a second image at a second point in time that is later than the first point in time;
   iii) coloring the first image by a first color to create a first colorized image;
   iv) coloring the second image by a second color to create a second colorized image;
   v) aligning the first and the second colorized images so that the first and second colorized images are congruent;
   vi) summating the congruently aligned first and second colorized images to create a multicolor image showing colors created by the summation of the first and second color;
   vii) taking a third image at a third point in time that is later than the second point in time;
   viii) coloring the third image by a third color to create a third colorized image;
   ix) aligning the first, second and third colorized images so that the first, second and third colorized images are congruent; and
   x) summating the congruently aligned first, second and third colorized images to create a multicolor image showing colors created by the summation of the first, second and third colors.

2. The method according to claim 1, wherein the first color is red and the second color is blue.

3. The method according to claim 1, wherein the first color is red, the second color is blue, and the third color is green.

4. The method according to claim 3, wherein no additional images beyond the first, second and third colorized images are summated.

5. The method according to claim 1, wherein the entire respective images are colorized by the respective colors.

6. The method according to claim 1, wherein the summation of the colorized images is a plain summation without applying any other mathematical algorithms such as calculation of histograms, deconvolution, or application of calculus.

7. The method according to claim 1, wherein the images are taken at subsequent points in time that are between 1 and 10 seconds apart from each other.

8. The method according to claim 1, further comprising injection of a contrast agent prior to performing any of the steps i) through x).

9. The method according to claim 8, wherein the method is applied in one of a group consisting of: CT angiograms, catheter angiograms, MR angiograms, barium studies, interventional fluoroscopic procedures that use contrast, and ultrasound with the use of ultrasound contrast.

10. The method according to claim 1, wherein the method is an interventional fluoroscopic procedure including devices that are visible on X-ray.

11. The method according to claim 1, wherein the method is an ultrasound procedure in connection with motion.

12. The method according to claim 1, wherein the method is applied in dynamic systems that do not use injected contrast agents.

13. The method according to claim 12, wherein the method is applied in MRI techniques making moving blood or CSF visible.

14. The method according to claim 9, wherein
   the method is applied to a gray scale image where each gray pixel is created by subpixels of red, green, and blue light of different intensity levels of less than 100 percent luminosity resulting in gray rather than white as would be the case if all intensities are set at a 100 percent luminosity, wherein
   for coloring the first image red, a computer program coloring algorithm turns off the blue and green subpixels by setting blue and green subpixel light intensities to zero;
   for coloring the second image blue, a computer program coloring algorithm turns off the red and green subpixels by setting red and green subpixel light intensities to zero; and
   for coloring the third image green, a computer program coloring algorithm turns off the red and blue subpixels by setting red and blue subpixel light intensities to zero.

15. A system for taking and processing images for demonstrating blood flow in a chosen area in a patient by generating a color-coded multicolor image demonstrating such blood flow, said system comprising:
   an imaging device configured to take images of the chosen area in a patient including at least a first image at a first point in time and a second image at a second point in time, wherein the first and second points in time are set apart by 1 s-10 s;
   a computer programmed to:
      color the first image with a first color to create a first colorized image and the second image with a second color to create a second colorized image;

align the first and the second colorized images so that the first and second colorized images are congruent; and summate the congruently aligned first and second colorized images generating a multicolor image showing colors created by the summation of the first and second color; and a display device displaying the multicolor image; wherein said imaging device is configured to take a third image at a third point in time that is set apart from second int in time by 1 s-10 s; and said computer is further programmed to:

color the third image with a third color to create a third colorized image;

align the first, second and third colorized images so that all 3 images are congruent; and summate the congruently aligned 3 colorized images generating a multicolor image showing the first, second and third colors and colors created by the summation.

16. The system according to claim 15, wherein the computer is programmed to color the first image red and the second image blue.

17. The system according to claim 15, wherein the computer is programmed to color the first image red, the second image blue and the third image green.

18. The system according to claim 17, wherein the computer is programmed to summate just the first, second and third colorized images and no additional images and to color all three images in their entirety by the respective colors.

19. The system according to claim 15, wherein the summation of the colorized images is a plain summation without applying any other mathematical algorithms such as calculation of histograms, deconvolution, or application of calculus.

20. The system according to claim 15, further comprising an injection apparatus configured to inject a contrast agent into the patient prior to taking images by the imaging device.

21. The system according to claim 20, wherein the imaging device is one of a group consisting of: CT angiogram imaging device, catheter angiogram imaging device, MR angiogram imaging device, barium studies imaging device, interventional fluoroscopic procedures imaging device that use contrast, and ultrasound imaging device with the use of ultrasound contrast.

22. The system according to claim 15, wherein the imaging device is an interventional fluoroscopic procedure imaging device including devices that are visible on X-ray.

23. The system according to claim 15, wherein the imaging device is an ultrasound procedure imaging device configured to image in connection with motion.

24. The system according to claim 15, wherein the imaging device is applied in dynamic systems that do not use injected contrast agents.

25. The system according to claim 24, wherein the imaging device is an MRI imaging device configured to making moving blood or CSF visible.

26. The system according to claim 17, wherein the method is applied to a gray scale image where each gray pixel is created by subpixels of red, green, and blue light of different intensity levels of less than 100 percent luminosity resulting in gray rather than white as would be the case if all intensities are set at a 100 percent luminosity, wherein the computer is further programmed to perform a computer program coloring algorithm for coloring said first, second and third images by:

for coloring the first image red, said computer program coloring algorithm turning off the blue and green subpixels by setting blue and green subpixel light intensities to zero;

for coloring the second image blue, said computer program coloring algorithm turning off the red and green subpixels by setting red and green subpixel light intensities to zero; and for coloring the third image green, said computer program coloring algorithm turning off the red and blue subpixels by setting red and blue subpixel light intensities to zero.

* * * * *